United States Patent [19]

Hussein et al.

[11] Patent Number: 4,662,368

[45] Date of Patent: May 5, 1987

[54] LOCALIZED HEAT APPLYING MEDICAL DEVICE

[75] Inventors: Hany M. G. Hussein, Costa Mesa; Marvin P. Loeb; Stanislaw Sulek, both of Huntington Beach, all of Calif.

[73] Assignee: Trimedyne Laser Systems, Inc., Santa Ana, Calif.

[21] Appl. No.: 750,683

[22] Filed: Jun. 28, 1985

Related U.S. Application Data

[63] Continuation-in-part of Ser. No. 503,783, Jun. 13, 1983.

[51] Int. Cl.$^4$ ............................................. A61B 17/36
[52] U.S. Cl. ..................................... 128/303.1; 128/398
[58] Field of Search ........... 128/303.1, 303.11, 303.12, 128/303.13, 303.17, 401, 341, 398, 784, 656, 657, 303.15; 604/95

[56] References Cited

U.S. PATENT DOCUMENTS

| | | | |
|---|---|---|---|
| 2,047,535 | 7/1936 | Wappler | 128/784 |
| 3,136,310 | 1/1960 | Meltzer | 128/398 |
| 3,369,549 | 10/1965 | Armao | 128/303.1 |
| 3,941,119 | 3/1976 | Corrales | 604/95 |
| 3,957,055 | 5/1976 | Linder et al. | 128/341 |
| 4,033,331 | 7/1977 | Guss et al. | 128/657 |
| 4,074,718 | 2/1978 | Morrison, Jr. | 128/303.14 |
| 4,209,017 | 6/1980 | Shaw | 128/303.1 |
| 4,233,493 | 11/1980 | Nath | 128/303.1 |
| 4,266,549 | 5/1981 | Kimura | 128/303.1 |
| 4,423,726 | 1/1984 | Imagawa et al. | 128/303.1 |
| 4,437,474 | 3/1984 | Peers-Trevarton | 128/784 |
| 4,445,892 | 5/1984 | Hussein et al. | 128/344 |
| 4,448,188 | 5/1984 | Loeb | 128/303.1 |
| 4,449,528 | 5/1984 | Anth et al. | 128/303.1 |

FOREIGN PATENT DOCUMENTS

| | | | |
|---|---|---|---|
| 2826383 | 12/1979 | Fed. Rep. of Germany | 128/303.1 |
| 2829516 | 1/1980 | Fed. Rep. of Germany | 128/303.1 |

OTHER PUBLICATIONS

Protell et al., "The Heater Probe" Gastroenterology 74: 257-262 (1978).
Translation of Eichler et al., 28 26 383.

Primary Examiner—Kyle L. Howell
Assistant Examiner—Randy Citrin

[57] ABSTRACT

A medical device for applying localized heat to a site in a patient's body is described. The device includes a radiant energy transmitting conduit, e.g., a fiber optic, and a heat generating element which converts the transmitted radiant energy into heat. A suitable exterior guide member can also be provided for positioning the heat generating element. An opening can be provided in the heat generating element to enable a portion of the radiant energy to impinge directly upon the site. The medical device can be used to cauterize or destroy tissue, or to alter or remove undesirable deposits from lumens. The medical device can also serve as part of a system which provides the radiant energy and measures the temperature of the heat generating element while within the patient.

21 Claims, 17 Drawing Figures

LOCALIZED HEAT APPLYING MEDICAL DEVICE

CROSS-REFERENCE TO RELATED APPLICATION

This application is a continuation-in-part of copending application U.S. Ser. No. 503,783, filed on June 13, 1983.

TECHNICAL FIELD OF THE INVENTION

This invention relates to medical devices and procedures for applying localized heat to a site in a patient's body for such purposes as removing tissue or deposits or cauterizing tissue.

BACKGROUND OF THE INVENTION

Providing localized heat to a site in a patient's body has often been used to cauterize a lesion to stop bleeding. Localized heat can also be used to alter, remove, or destroy tissue in a patient's body. One example of such localized heating is the treatment of a bleeding ulcer. An endoscope is inserted through a patient's esophagus to view the bleeding site and direct an electric powered heating element to contact the site and cauterize the bleeding. Another example is the use of such heat to remove neoplastic pulmonary tissue.

Unfortunately, electric heating elements can be difficult to manipulate and generally heat up relatively slowly. The heating rate and maximum sustainable temperature is limited by the electric current available to the element. The available current in turn is limited by the size of the wires leading to the element. Wire size limits access to body sites for two reasons: larger wires cannot be inserted into small areas and increased wire size also means a loss of flexibility.

The electric current passing through the wires also limits the regions in the body in which such a device can be used. There is the threat of an electric shock to the patient and the generated field about the wires by flowing current can also have undesirable effects. One region where such electric currents and fields could possibly be life threatening is in the heart.

One proposal which heats the end of an endoscope to avoid dew forming on a window is shown in U.S. Pat. No. 4,279,246 to Chikama. That device heats the window to about body temperature to prevent dew formation. However, due to the design of the device, the heat generated on the window is limited to about body temperature and therefore could not be used to alter or destroy tissue.

Cardiovascular disease continues to be an ongoing problem, particularly in complex societies. It has been estimated that every year more than one-half million Americans die from cardiovascular disease. Another 3.5 million are believed to suffer some degree of incapacitation because of this disease. A particularly serious problem is the progressive blockage of a blood vessel by the collection or deposit of fatty material such as arteriosclerotic plaque. The collected material at first constricts the vessel, reducing blood flow to a relatively small channel. Eventually, blood flow can be obstructed completely.

Various devices and methods have been proposed in an attempt to deal with obstructed or constricted blood vessels. In one method, a balloon is positioned within the constricted channel and inflated, compressing the plaque into the vessel walls to widen the opening. This method is only available when the constriction in the blood vessel is not so severe that the remaining channel is too small for the deflated balloon. Compression of the plaque into the vessel walls is not possible where the plaque has become calcified and hard. Such a method is not even attempted in completely obstructed vessels. Applying radial stress to vessel wall also results in excessive and permanent deformation of this wall and subsequent loss of its integrity.

Accordingly, it would be desirable to provide a method and device which avoids the shortcomings of the prior art yet provides an effective means for delivering localized heat to a site within a patient's body. The heat provided by such a device can be used to stop bleeding or remove body tissue or material in a blood vessel, even a completely obstructed blood vessel. For such a device, the heat should be quickly developed without use of electrical current. Also, the device should be sufficiently small so that it can be directed into a patient's body cavity or lumen such as a blood vessel. It would also be desirable to provide rapid and accurate measurement of the heat produced. The present invention meets these desires.

SUMMARY OF THE INVENTION

The present invention contemplates a medical device, system and method for applying localized heat to a site in a patient's body. The localized heat provided in accordance with the present invention can be used for several purposes such as cauterizing a lesion to stop bleeding, or to remove a clot, or to remove an arteriosclerotic deposit from a blood vessel. The heat available can also be used to create an open channel in a previously occluded blood vessel.

Generally, the medical device embodying this invention includes a heat generating element mounted on the distal end of an elongated electro-magnetic energy transmitting conduit or member. A preferred conduit is a single flexible quartz optical fiber. Electro-magnetic energy in the form of visible light from an intense light source, such as a laser, an be transmitted through the conduit and emitted onto a light receiving surface of the heat generating element. The light is converted by the element to heat. The element can then be contacted with a material in a patient's body such as a clot, deposit or tissue to alter that material by melting, removing or destroying it. The heat generating element preferably has a rounded exterior surface end and is retained on the conduit by a locking means, such as a ridge on the element received in a complementary groove on the conduit.

Since light is used to transfer energy to the heat generating element, there are no electrical currents present which could possibly threaten the patient. Also, far more energy can be conducted by light through an optical fiber than by electricity through wires of the same diameter. The use of an intense light from a laser allows a substantial amount of energy to be rapidly transferred to the heat generating element for rapid heating. This avoids the difficulties inherent in electrical systems, including the presence of electrical currents and the relatively slow heating rate of the element.

In one embodiment of the present medical device an elongated guide wire can be selectively positioned within the lumen in association with the heat generating element. To this end, the heat generating element can include an elongated channel, e.g., a slot or bore, for slidably receiving the external guide wire situated along the light transmitting conduit. The heat generating element, with the attached light transmitting fiber, can be slid along the guide wire until a selected region of the lumen has been reached. The light source can then be activated, and the heat generated by the heating element applied to a contiguous region of the lumen.

In yet another embodiment of the medical device, usable with or without the guide wire, the heat generating element has a central aperture or bore which permits a portion of the light transmitted to the heat generating element to pass through the aperture and directly impinge upon a selected region of the plaque obstruction. With this form of heat generating element, both radiant and heat energy can be applied sequentially or simultaneously to the lumen or to the obstruction therein.

The heat generating element can have an eliptical cross-section. Such a cross-section readily slides into and through the lumen(s). In the eliptical cross-section also minimizes the accumulation of cellular material on the distal end of the heat generating element.

The heat generating element can also include a vent or escape port that permits gases formed therein to escape from within that element. The gas escape port can be located adjacent the region where the heat generating element is coupled to the light transmitting fiber.

The medical device can be used as part of a system which also includes a light source for providing sufficient light energy to raise the temperature of the heat generating element sufficiently to soften a plaque deposit or the like in a blood vessel, as well as a temperature sensing means associated with the light transmitting conduit for monitoring the temperature of the element. The preferred light source is a laser and the preferred temperature sensing means is a pyrometer. Other such means can be utilized, however. The laser is activated to transmit an intense light pulse through the conduit. The light is emitted by the conduit onto the receiving surface of the heat generating element which converts the light energy into heat. When the laser is deactivated, the light or glow from the hot element is transmitted back through the light transmitting conduit. This glow could then be converted by the pyrometer into a temperature reading or measurement.

The medical device can also be provided with an elongated tube which carries the light transmitting conduit. The heat generating element extends beyond the distal portion of the tube so it may be brought into contact with the tissue or deposit to be heated. The tube helps guide the conduit to the desired location and is particularly useful for providing access to a blood vessel. The exterior of the tube can be provided with blood flow occlusion means such as an inflatable balloon to selectively stop the flow of blood. A fluid such as saline, a radiopaque liquid or carbon dioxide can also be introduced through a passageway defined by the tube.

A viewing system to permit viewing within the lumen or blood vessel can also be provided as part of the medical device. Generally, the viewing system includes a fiberoptic viewing bundle carried by the tube to provide a view of the heat generating element and the tissue or obstruction about to be contacted. A suitable clear flushing fluid can be introduced through the passageway defined by the tube to provide improved viewing.

In use, the medical device is inserted into a patient's body such as by positioning the distal end of the medical device within a blood vessel. The element is contacted with a site such as a constriction, and light energy is transmitted through the conduit to heat the element rapidly and sufficiently to soften and open at least a portion of the constriction as the element contacts the constriction and is urged forward. In one preferred method aspect, the blood flow is occluded by the balloon and a radiopaque liquid is introduced into the vessel to allow fluoroscopic study of the constriction and location of the medical device. A bubble of biologically compatible gas such as carbon dioxide can be introduced into the vessel about the element prior to the light transmission and attendant heating. This avoids dissipation of heat into the liquid or blood otherwise in contact with the element.

A method of removing vascular obstructions and recanalizing an occuluded vascular member is also provided. The method includes the steps of:

Moving a heat generating element through the vascular system and positioning that element in a selected vascular member in contact with the occulsion;

transmitting electro-magnetic, radiant, energy through an elongated fiberoptic transmitting member to the heat generating element;

heating the heat generating element with the radiant energy;

conducting heat from a circumferential region of the heat generating element to a corresponding circumferential region of the occlusion in contact with that element; and sliding the heat generating element into and through the occlusion to recanalize the vascular member.

Numerous other advantages and features of the present invention will be readily apparent to those skilled in the art from the following detailed description of the preferred embodiments of the invention, the drawings, and the appended claims.

DESCRIPTION OF THE PREFERRED EMBODIMENTS

While this invention can be embodied in many different forms, there are shown in the drawings and described in detail, preferred embodiments of the invention. The present disclosure is an exemplification of the principles of the invention and is not intended to limit the invention to the embodiments illustrated.

The present invention is a medical device for delivering and applying localized heat to a site in a patient's body. The heat can be used to stop bleeding or remove or alter a material such as tissue or deposit in the body. The material being altered can be any solid or semi-solid substance found in the body including living tissue or deposits such as clots, fat or arteriosclerotic plaque.

Figures 1, 2:
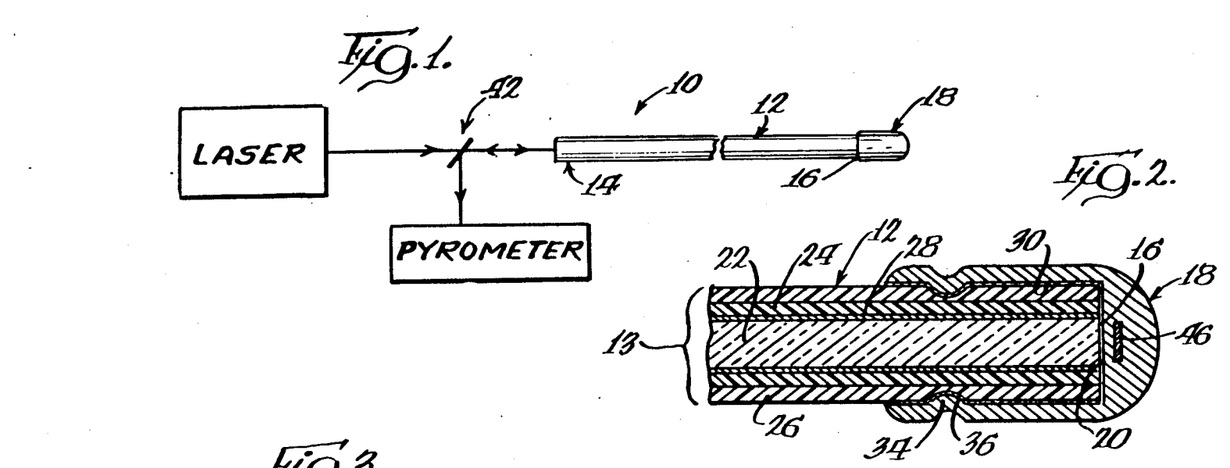
FIG. 1 is a schematic view of a system including a medical device embodying the present invention.
FIG. 2 is an enlarged cross-sectional elevational view of the distal end portion of the medical device of FIG. 1.

FIGS. 1 and 2 show a medical device 10 embodying the present invention and including an elongated electro-magnetic energy transmitting member 12 the member 12 can be an optical fiber, a microwave channel or waveguide, having a proximal end 14 and a distal end 16. If the member 12 is an optical fiber, radiant energy in the form of light can be transmitted by it. A heat generating element 18 is mounted with respect to the distal end 16 of the member 12 such that light or like radiant energy transmitted by the fiber is absorbed and converted by the element into heat. The light is emitted by the distal end 16 of the conduit and is received and collected by a light receiving surface 20 on the element 18. The element 18 is preferably mounted on the distal end 16 of the conduit 12 and retained in that position by appropriate means discussed in more detail below. Mounting the element 18 directly on the conduit 12 insures that the light is properly delivered and the element will not become disengaged from the conduit.

The conduit 12 is preferably a single, flexible light-transmitting fiber such as used in fiberoptic devices and generally has a total exterior diameter of about one millimeter or less. A single fiber generally has the rigidity needed to press the element into a deposit or tissue. Larger or smaller fibers can be used depending on the available area in a patient. Generally, the single, light-transmitting fiber 13 includes a fiber core 22 surrounded by cladding 28. The internal reflection caused by the cladding 28 should be such that the fiber 13 has a low divergence as the light exits the distal end 16. The core 22 is made of glass, e.g. silica quartz. The cladding 28 is made of silicone, plastic or silica. The core 22 and cladding 28 have a combined diameter of less than about 0.5 millimeter to about 1.0 millimeter. Substantially all of the light exiting the distal end 16 should be directed forward to be absorbed by the light receiving surface 20. This generates the majority of the heat at the forward end of the heat generating element 18 where it is needed while minimizing the heat on the rearward portions of the element where it could otherwise be detrimental to the fiber 13.

To protect the fiber core 22 and cladding 28, the fiber also includes a jacket 26 which surrounds the cladding 28 and is held in place by a resin coating 24. The external jacket 26 is usually made of a flexible plastic material such as poly(ethylene) or poly(tetrafluoroethylene). This also provides a flexible and smooth surface allowing easy manipulation of the medical device. Fiber optic bundles are not prefered since the adhesive between individual fibers limits the amount of light which can be transmitted without melting of the bundle.

The conduit 12 should be flexible yet sufficiently resilient so that it is possible to push the conduit along a lumen to drive the heat generating element 18 into and through an obstruction. One such suitable conduit is a fiber optic having a core diameter of 0.4 millimeters which is marketed under the trademark Med 400 by Quartz Products Corporation of Plainfield, N.J.

The forward portion of the heat generating element 18 is preferably generally rounded on its exterior surface to facilitate pressing the element into and through softened body material while minimizing the risk of mechanical perforation. The heat generating element can alternatively have other shapes as desired including oblong or eccentric with respect to the axis of the fiber or even generally crescent-shaped. Such an eccentric or oblong shape can be rotated to generate an even larger channel through an obstruction. A crescent-shaped element allows for fluid flow and viewing past the element.

The element 18 is preferably made of metal such as surgical stainless steel, but could also be made of a combination of thermally conductive and insulating material such as metal and ceramic. The inside light receiving surface 20 is preferably treated, e.g., oxidized, to increase its coefficient of emissivity to about 0.95 or greater to further increase the absorption of light by the element 18. Alternatively, the surface 20 can be treated by being coated by a material having a high coefficient of emissivity such as lamp or carbon black. The exterior surface of the heat generating element 18 is preferably coated with a non-stick or release surface such as poly(tetrafluoroethylene) to provide easy release from the tissue. Poly(tetrafluoroethylene) usually is used for operating temperatures below about 300 degrees C.

The distal end 16 of the conduit 12 is preferably positioned or received in cavity 30 defined by the rear portion of the heat generating element 18. The element 18 can be retained on the distal end 16 by appropriate means for mounting such as an adhesive, an appropriate locking means, or a combination of both. The locking means is preferably at least one inwardly extending, peripheral ridge 34 on the element 18 received in a complimentary groove 36 defined by the conduit 12. The groove 36 should extend into the jacket 26 but not into either the core 22 or the cladding 28. The adhesive such as hardened epoxy resin can be used to retain the element 18 on the conduit 12 while the ridges 34 are crimped into the groove. Since some adhesives may become ineffective under intense heat, the locking means provides a backup to ensure the element remains in place.

The heat generating element 18 has sufficient mass to avoid burn-through during use. However, the mass is not so great as to materially slow its heating rate. For this reason, it is advantageous to place the thickest portion of material in the forward portion of the element 18 where the radiant energy, e.g., light, impinges. A minimum amount of space between the distal end 16 of the fiber and the radiant energy receiving surface 20 of the element 18 reduces the presence of other matter such as air or liquid which, if present in excess may require venting due to expansion as a result of the heat generated. Where such a space is provided, one or more vents are supplied to provide communication between the space and the outside surface of the element to the ambient surroundings.

The distal end 16 of the fiber is preferably spaced no more than 2 diameters of the core 22 away from the light receiving surface 20. Where the core is about 0.5 millimeters, this spacing should be no more than about 1 millimeter. This relatively close spacing insures that substantially all of the light is received on the forward light receiving surface 20 and is not dispersed on the inside side walls of the cavity 30.

The medical device can serve as part of a system which, as shown in FIG. 1, includes a light source such as a laser associated with the proximal end 14 of the fiber 13. The light source is chosen to deliver sufficient light energy to raise the temperature of the element 18 above the body temperature of the patient to soften material causing an obstruction or to destroy tissue. The system further includes temperature sensing means such as a pyrometer also associated with the proximal end 14 of the fiber for measuring the temperature of the element 18. Both the light source and temperature sensing means can be associated with the proximal end 14 of the fiber 13 by a beam splitting means 42. The beam splitting means 42 can be a partial mirror or a system such as a rotating or movable mirror. When the mirror is in a first position the laser light is directed into the fiber 13. After the laser is deactivated, the mirror is then placed in a second position to direct the resulting radiation or glow of the element 18 emitted by the fiber proximal end 14 to the pyrometer. A thermocouple can be affixed to the heat generating element to sense temperature.

The laser produces the light which is converted by the heat generating element 18 into heat. The word light is used in its broad sense, meaning electromagnetic radiation which propagates through space and includes not only visible light, but also infrared, ultraviolet and microwave radiation. The laser is preferably activated simultaneously with the temperature measurement. By monitoring the glow of the heated element 18 it is also possible to provide an advance warning of approaching burn-through where the element 18 has been provided with a layer of different metallic or non-metallic material 46 embedded within the forward portion of the element 18.

The light can enter the fiber continuously or intermittently, as desired, to maintain the element 18 above a predetermined temperature such that it is capable of softening a plaque deposit or cauterizing bleeding tissue. Where the medical device is used in a blood vessel, rapid heating of the element 18 is preferred since this allows the softening and removal of obstructing material while minimizing the amount of heat transferred to the tissues surrounding the blood vessel. A slower heating rate releases a greater total amount of energy into the entire tissue area while a rapid heating rate releases less total energy, but concentrates it in a small area within the material to be softened and removed. The element can be first heated i.e., light transmission begun, and then contacted with the deposit. This minimizes heat dissipation into the surrounding tissue and allows the element to reach a higher temperature before contact.

Figure 3:
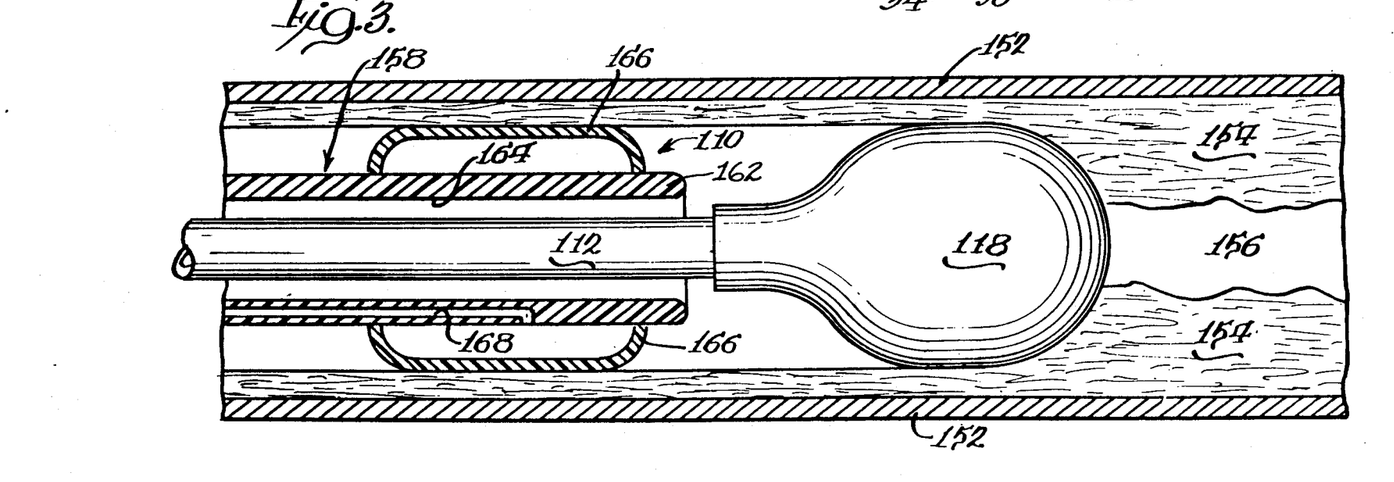
FIG. 3 is another enlarged elevational view, partly in section, of a further alternative embodiment of the medical device shown received, within a blood vessel having a constriction.

An alternative embodiment for the medical device 110 is shown in FIG. 3. The medical device is shown received within a blood vessel 152 having a deposit 154 which reduces the operative size of the blood vessel to a relatively small constricted channel 156. The medical device 110 includes a light transmitting conduit 112 and a heat generating element 118 substantially as described above. The element 118 includes an enlarged head portion to create a channel of relatively larger diameter in the deposit 154.

The medical device 110 also includes an elongated tube 158 having a proximal portion (not shown) and a distal portion 162 and defining a passageway 164 along its length. The elongated tube 158 allows for positioning the light transmitting conduit 112 and heated element 118 in a lumen such as blood vessel 152 by passing the tube through the skin and muscle layers of the patient into the blood vessel. The conduit 112 is slidingly received in the tube 158 so that it can be moved longitudinally with respect to the tube and the element 118 extended beyond the distal portion 162 of the tube. The element can be of such size that it may be received within the passageway 164 during the placement of the device within the blood vessel 152. The tube 158 is then first located in a vessel and a conduit 112 with a relatively small heated element as shown in FIG. 2 inserted into the tube 158.

Alternatively, the element 118 as shown in FIG. 3 can be relatively larger in cross section than the passageway 164 to create a larger channel in an obstruction. The heated element can even be larger than the outer diameter of the tube 158 allowing the tube to be advanced progressively as the element is repeatedly pressed forward to create a longer channel. When the heated element is larger in cross section than the passageway 164, the element can rest against the opening of the tube distal portion 162 during insertion into the blood vessel.

The defined annular passageway 164 permits the introduction of fluid into the blood vessel such as a radiopaque liquid which allows fluoroscopic study of the size and location of the deposit 154 and the constricted channel 156. The element 118, also radiopaque can also be fluoroscopically tracked. The conduit 112 and tube 158 can also be provided with radiopaque markings along their lengths for fluoroscopic tracking.

The tube 158 preferably carries a blood flow occlusion means such as an inflatable balloon 166 positioned circumferentially about the tube on the distal portion 162. The balloon 166 is preferably made of a suitable flexible plastic material and is inflated to contact and seal with the blood vessel wall by introducing a fluid such as carbon dioxide through a channel 168 defined by a thickened wall of the tube 158. After the blood vessel 152 has been occluded, a fluid such as a physiologically tolerable flushing liquid can be introduced through passageway 164. Suitable liquids include a saline solution, a dextrose solution, or an oxygen bearing liquid which provides oxygen to tissue downstream of the balloon. A radiopaque liquid can also be introduced for fluoroscopic viewing as described above. A physiologically tolerable gas such as carbon dioxide can also be introduced through the passageway 164 such that it surrounds the element 118 with a temporary gas bubble to minimize dissipation of heat from the element which otherwise would be directed into blood or radiopaque liquid. This also avoids damage to the blood. The gas bubble or introduced liquid can be withdrawn by suction through the passageway 164 after the procedure is over. Any debris generated can also be removed by suction.

Figure 4:
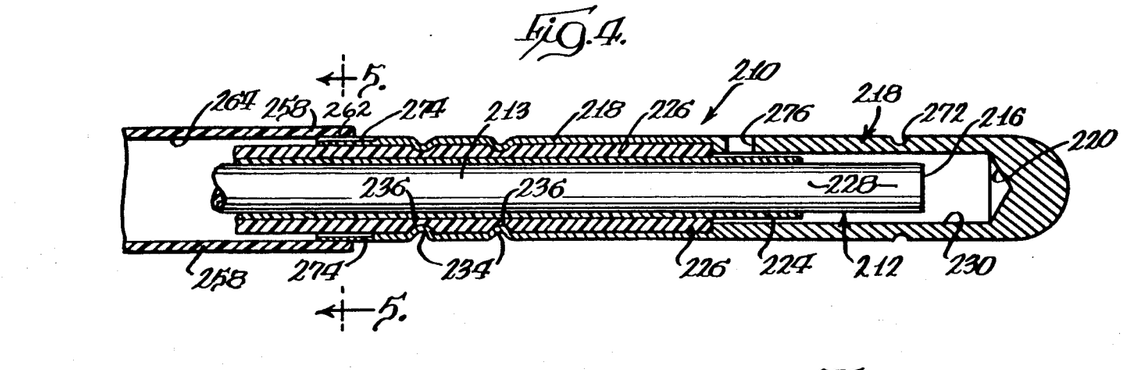
FIG. 4 is an enlarged elevational view, partly in section, of the distal end portion of a further alternative embodiment for the medical device.
Figure 5:
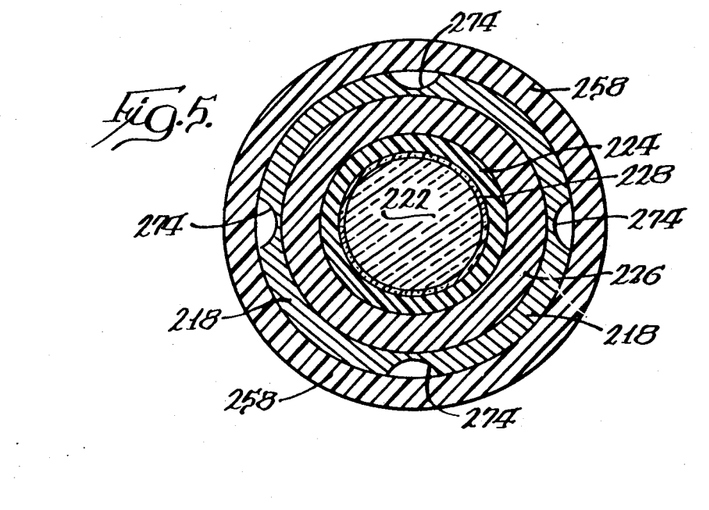
FIG. 5 is further enlarged cross-sectional view taken generally along plane 5—5 of FIG. 4 showing the internal structure of the medical device of FIG. 4.

A still further alternative embodiment for the medical device 210 is shown in FIGS. 4 and 5. As before, the heat generating element 218 is mounted on the distal end 216 of the light transmitting conduit 212. The resin coating 224 and jacket 226 have been trimmed back from the distal end 216 of the fiber 213 leaving a section of the clading 228 surrounding the fiber core 222 open to the sides.

The removal of the resin coating 224 and jacket 226 from the end portion of the fiber core 222 creates a spacing between the fiber core 222 and the element 218. The air in this space serves as an insulator between the element 218 and the fiber 213. Suitable other insulating materials can also be located between the element and fiber. Directing substantially all of the emitted light onto the light receiving surface 220 on the forward portion of the element 218 together with this spacing minimizes the conduction of heat from the element 218 to the jacket 226 of the conduit 212. To further limit the transfer of heat from the forward portion of the element 218 toward the rearward portion, a section of reduced metal thickness such as caused by a peripheral notch 272 can be provided. Because there is less metal in the area of the notch 272, a lesser cross-sectional area for heat conduction is available and there is less transfer of heat per unit time toward the rearward portion of the element 218.

The heat generating element 218 is retained on the conduit 212 by one or more inwardly extending ridges 234 received within corresponding peripheral grooves 236 in the jacket 226. The distal portion 262 of tube 258 engages the rear portion of the heat generating element 218 also to help retain the element on the conduit 212. The tube 258 can be made of the same material as the jacket 226, and is preferably a heat resisting plastic such as poly(tetrafluoroethylene). The tube 258 defines passageway 264 along its length through which the light transmitting conduit 212 is received.

The rear portion of the heat generating element 218 preferably defines at least one, and optimally a plurality of flutes 274 which are in fluid communication with the tube passageway 264. The flutes 274, together with the distal portion 262 of the tube, define openings through which a fluid such as carbon dioxide may be introduced through the passageway about the rear portion of the heat generating element 218. The introduced fluid is not only useful for clearing or removing debris produced about the heat generating element 218 when in use, but also helps to cool the rear portion of the element 218.

The elongated structure of the heat generating element 218 assists manipulation of the device 210 as when it is passed through a channel defined by an endoscope. To remove any gaseous material which may be generated within the cavity 230 defined by the heat generating element 218, a vent 276 can be provided on the side of the element in communication with the cavity 230.

Figures 6, 7, 8:
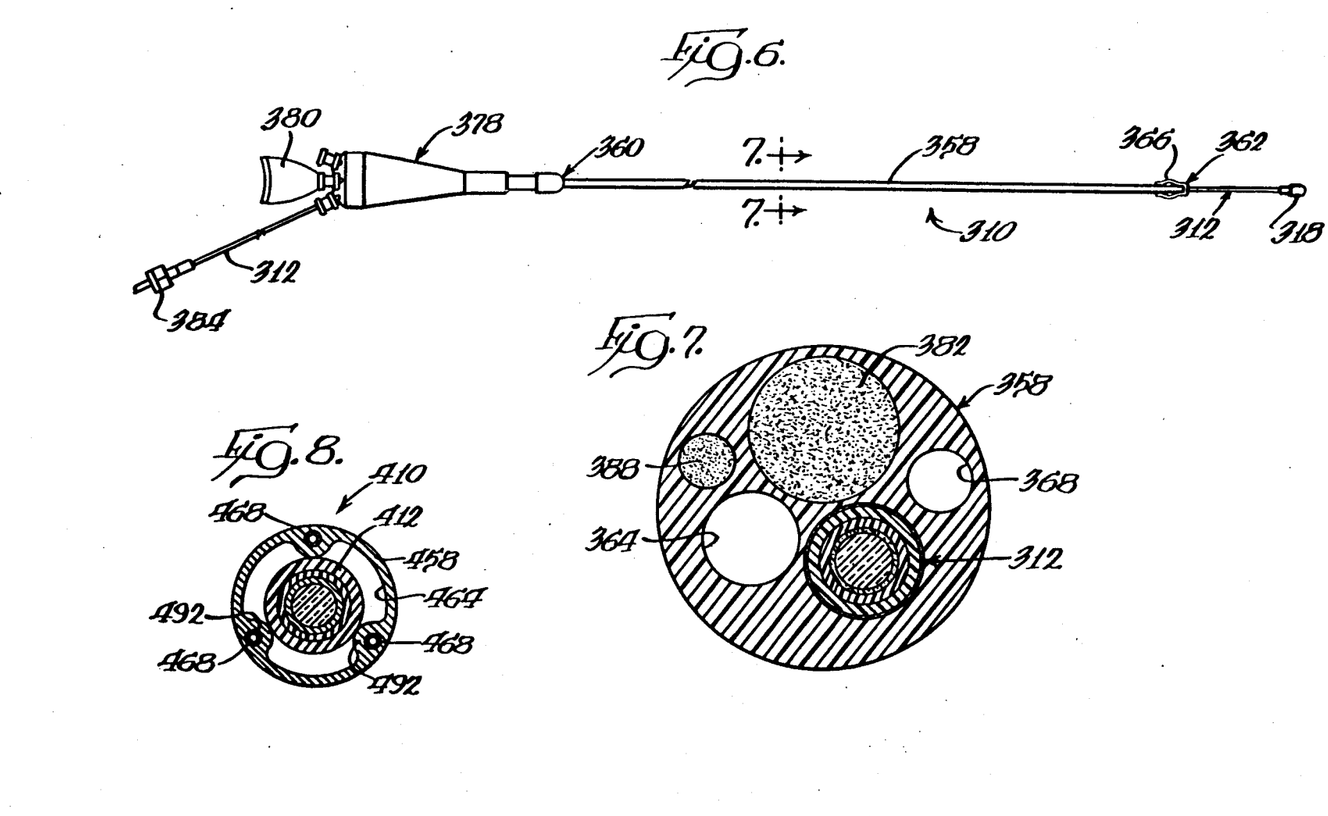
FIG. 6 is an elevational view of a further alternative embodiment for the medical device.
FIG. 7 is an enlarged cross-sectional view taken generally along plane 7—7 of FIG. 6 showing the internal structure of the medical device of FIG. 6.
FIG. 8 is a cross-sectional view of a still further embodiment for the medical device.

A still further embodiment for the medical device 310 is shown in FIGS. 6 and 7. In this embodiment, the medical device includes a heat generating element 318 mounted on the end of a light transmitting conduit 312 which is slidably received within an elongated tube 358. An inflatable balloon 366 is also included on the distal portion 362 of the tube 358. Mounted on the proximal portion 360 of the tube is an assembly including an eyepiece 380 that forms part of a viewing system. The viewing system also includes a fiberoptic viewing conduit 382 and illumination conduit 388 carried by the tube 358 together with the appropriate lens devices well-known in the art carried both by the assembly 378 and the distal end 362 of the tube.

The conduit 312 is slidably carried by the tube 358 and includes a connector 384 on its proximal end for linking with appropriate laser. The tube 358 also defines a channel 368 for inflating the balloon 366 and a flushing or suction passageway 364 for introducing fluids into a lumen. The passageway 364 can also be used in conjunction with a guide wire to direct the device into the patient.

In use, the distal portion of the medical device is inserted into a patient and positioned in the approximate desired location. The balloon 366 is then inflated to occlude the blood vessel. A clear fluid such as carbon dioxide or a liquid can then be introduced through the passageway 364 to allow viewing through the viewing system. Appropriate means can also be provided to wash the distal end of the viewing system. This allows visualization of the occlusion to be made prior to contact with the heat generating element 318 and also to determine the size of the size of the channel which has been opened by the heat generating element after it has been withdrawn.

As still further embodiment for the medical device 410 is shown in FIG. 8. The light transmitting conduit 412 extends through the elongated tube 458 and is centered within the defined passageway 464 along the central axis of the tube by centering means such as three longitudinal ridges 492 extending inward from the tube wall. Each ridge 492 preferably defines a channel 468 which can be used to inflate a balloon on the tube or for introduction of fluid through the distal end of the tube. The ridges 492 can be extrusion molded unitary with the remainder of the tube 458.

The ridges 492 center the conduit 412 and the element mounted on its distal end so that the element can be directed into the center of a lumen and avoid the lumen walls. The ridges 492 also minimize heat transfer from the conduit 412 to the tube 458 and hence to the lumen. The flow of a fluid through the passageway 464 about the conduit 412 also lowers its temperature during use.

The preferred lasers are Argon and Neodyminum-YAG. Tests were done with a Med 400 fiber optic (0.4 millimeter diameter core) 1.8 meters in length and equiped with a stainless steel heat generating element having the configuration as shown in FIG. 4 and a length of about 9 millimeters, a diameter of about 1.0 millimeters, and a mass of about 0.1 grams. In air, a 68 watt Neodyminum-YAG laser manufactured by Messerschmidt of Munich, West Germany raised the temperature of the heat generating element from room temperature to about 500 degrees C. in about 0.5 seconds. Similarly, in air, a 6 watt Argon laser manufactured by Laser Ionics of Orlando, Fla. raised the temperature of the heat generating element to 654 degrees C. from a base line temperature of 25 degrees C. in five seconds. A two second burst from a 6 watt Argon laser raised the temperature of the heat generating element to 231 degrees from a base line temperature of 24 degrees C.

Measurements of laser intensity were made at the proximal end of the fiber optic by using a laser power meter Model 201 made by Coherent Radiation of Palo Alto, Calif. Temperature measurements of the element were made using a 30 gauge Model HPY-1 hypodermic thermocouple available from Omega Engineering of Stanford, Conn. and a digital temperature meter available from Analogic Corporation of Wakefield, Mass.

Tests were also made of the energy transfer by the device into liquid samples using both blood and tap water samples. Blood was withdrawn from several patients in a process which mixed approximately 7 milliliters of blood with 0.07 milliliters of 15 percent ethylene diamine tetraacetic acid (EDTA). The blood was pooled by mixing to obtain a uniform larger quantity. Conical polystyrene sample cups having a capacity of 2.0 milliliters were divided into two groups and filled respectively with 0.5 milliliters of tap water for 0.5 milliliters of blood.

The heat generating element was then immersed in the water or blood together with the thermocouple temperature probe. Tests were then made at 1 to 6 watts with an Argon laser for periods of 10 to 60 seconds to determine the heat generation of the device. Seven samples were tested for each combination of energy and time. The base line temperature for each test was 19-20 degrees C.

A 10 second burst of laser energy at 1 watt intensity raised the temperature of the water samples to an average of 33 degrees C. and the blood samples to an average of 46 degrees C. A 1 watt burst for 60 seconds raised the temperature of the water samples to an average of 52 degrees C. and blood to an average temperature of 66 degrees C.

Using a 6 watt Argon laser, a 10 second burst raised the temperature of the water samples to an average of 52 degrees C., and a 30 second burst raised the temperature of the water to an average of 87 degrees C., and a 60 second burst raised the temperature to an average of 98 degrees C. No tests were made with blood at a greater than 1 watt intensity.

Figure 9:
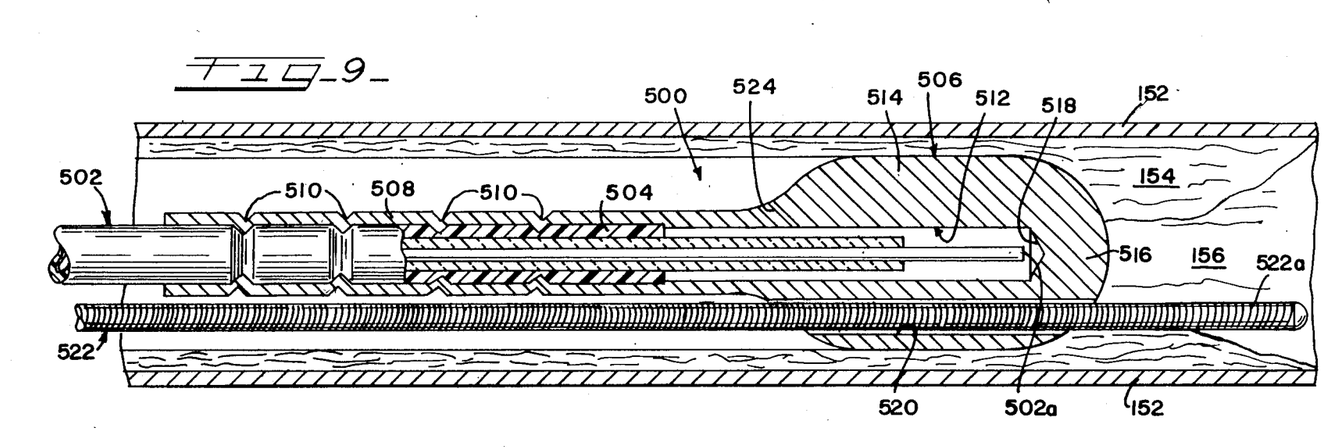
FIG. 9 is an enlarged cross-sectional view of another embodiment of the medical device shown received within a blood vessel that has a constriction therein.

FIG. 9 illustrates an alternative embodiment of the medical device 10 as generally depicted in FIG. 1. The distal portion of medical device 500 is shown in FIG. 9 as an enlarged, fragmentary, sectional view. This portion of medical device 500 can be coupled to the remainder of the system shown in FIG. 1 as described hereinabove. Medical device 500 includes a light transmitting fiber or conduit 502, of the same general nature as those utilized in the previously described embodiments of this invention, and a heat generating element 506 that is energized by a light beam that emanates from conduit 502 at its distal end 504.

The heat generating element 506 is constituted by a bulbous head portion 516, body portion 514 and a unitary sleeve portion 508 that together define a central cavity 512. Heat generating element 506 is mechanically coupled to conduit 502 at its distal end 504 by means of a plurality of peripheral mechanical crimps 510 in sleeve portion 508 which crimps correspond to the locking means 34 and 36 shown in FIG. 2. If desired, an adhesive can also be applied between the distal end 504 and the region of sleeve portion 508 bounded by mechanical crimps 510.

The wall thickness of the body portion 514 can be the same as or less than the wall thickness of the head portion 516. Preferably, the wall thickness of the body portion 514 is less than that of head portion 516 so as to concentrate more of the generated heat into the head portion 516 as discussed hereinabove with reference to the embodiment of FIG. 2.

The heat generating member 506 receives radiant, or light energy through the optical fiber 502. The radiant energy impinges on at least an end surface or surfaces 518 that define cavity 512. The radiant energy impinging on the surface is 518 is converted to localized heat as discussed previously with respect to the previously illustrated embodiments. The generated heat is then transferred primarily by conduction, to the lumen obstruction 154.

The heat generating member 506 is assymetrical. An elongated channel 520 is formed in body portion 514 substantially parallel to the longitudinal axis of member 506. The channel 520 can be a cylindrical boring formed in the side wall 514 and the end 516. Alternately, the channel 520 can be a generally U-shaped slot. The channel 520 slidably engages and receives a flexible guide wire 522 of a selected size and shape. The guide wire 522 can be of the type generally used with devices that are insertable into the human vascular system. In FIG. 9, the distal end 522a of the guide wire 522 is illustrated as extending beyond the obstruction 154. Even if the obstruction 154 is such as to block movement of the distal end 522a, the heat generating element 506 may still be used. The exact position of the distal end 522a is not a limitation of the present invention.

The elongated channel 520 is usually slidably engaged with the flexible guide wire 522 after the guide wire has been positioned within a selected lumen of the patient. The heat generating element 506 is then slid along the guide wire 522, via cooperation between the channel 520 and the guide wire 522. When positioned, as discussed previously, radiant energy is applied through the light transmitting conduit 502 which in turn heats the heat generating element 506.

The heat generating element 506 also includes a gas vent port 524 formed in body portion 514 adjacent the sleeve portion 508. The vent 524 provides for the escape or ventilation of gases formed in the cavity 512 as a result of the radiant energy applied to the heating element 506 through conduit 502. The vent 524 places the cavity 512 in fluid flow communication with the interior of the lumen into which the heating element 506 has been positioned. While the escape port or vent 524 may be formed in the body portion 514 at any convenient location. Placing the vent 524 at about the juncture of sleeve portion 508 and the body portion 514 as illustrated in FIG. 9 insures that any escaping, relatively hot gases do not impinge directly upon the surrounding lumen but instead are diffused.

Figure 10:
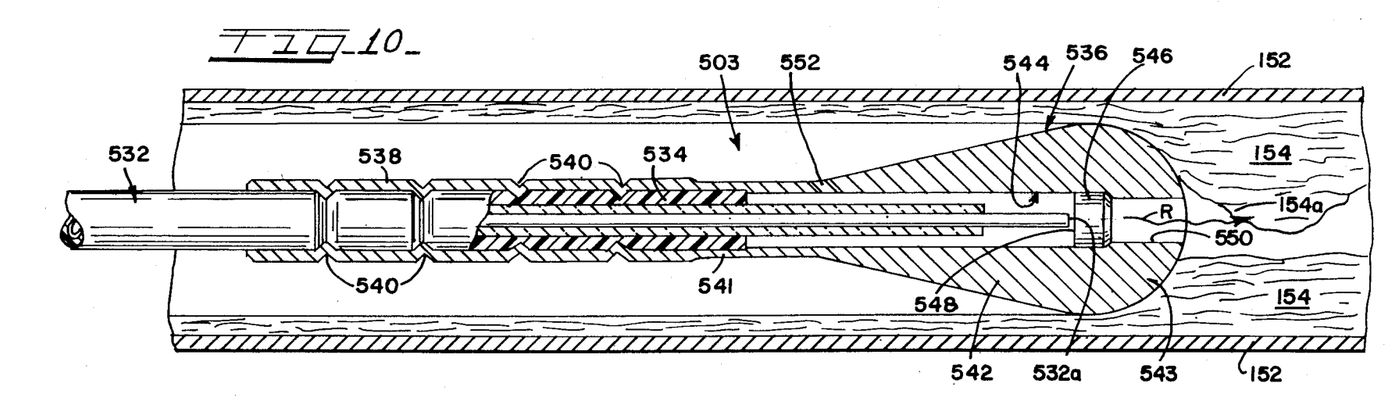
FIG. 10 is an enlarged cross-sectional view of still another embodiment of the medical device shown received within a blood vessel that has a constriction therein.

FIG. 10 illustrates another embodiment of the medical device 10 of FIG. 1. The medical device 530 shown in FIG. 10 in an enlarged, sectional, fragmentary view can be coupled to the other elements of the medical device 10 of FIG. 1. The medical device 530 includes an elongated light conducting or transmitting conduit 532 with a distal end 534 and heat generating element 536.

The distal end 534 is coupled to the heat generating element 536 at sleeve portion 538 by a plurality of mechanical crimps 540. In addition, adhesive may be used between the sleeve portion 538 and the distal end 534. The sleeve portion 538 is unitary with an elongated neck portion 541 that merges into a tapered body portion 542. The body portion 542 in turn terminates in a bulbons or rounded head portion 543. As illustrated in FIG. 10, tapered body portion 542 has a varying side wall thickness and partly defines a cavity 544. An optically transparent means such as a lens or window 546 is positioned within the head portion 543 so as to block the distal end of the cavity 544 against the inflow of body fluids and tissue components. The window 546 can be made of quartz, sapphire or other optically transparent material. Aperture or bore 550 in head portion 543 defines a communication port between the window 546 and the surroundings. The window 546 prevents bodily fluids or material that have entered the boring 550 from contaminating the end 532a of the fiber optic member 532. The thickness of the side wall of body portion 542 is less than the wall thickness of the head portion 543.

The light transmitting fiber 532 emits light or radiant energy from an end surface 532a which impinges upon a surface 548 of the window 546. As discussed earlier with respect to the embodiments of FIGS. 1–8, radiant energy transmitted through the conduit 532 heats the heat generating element 536 when it impinges upon the surface 548. A portion of the radiant energy, such as the light beam designated by the legend R emitted from the surface 532a passes through the window 546 and the aperture 550 directly into the surrounding lumen. The radiant energy R then impinges upon a surface 154a of the obstruction 154. The sequential or simultaneous application of heat and radiant energy to the obstruction 154 softens or vaporizes the plaque thereby easing the advance of the heat generating element 536.

As a result of adding the port or aperature 550, light or electromagnetic energy as well as thermal energy, are sequentially or simultaneously applied to the obstruction 154 desired to be removed. By controlling the size of the aperture 550, it is possible to control the amount of power or energy delivered directly to the site.

The heat generating element 536 also includes a gas vent, or port 552. The vent or port 552 extends through the body portion 542 of the hollow heat generating element 536. The vent 552 provides an escape aperture for gases that may develop in the cavity 544.

With respect to the exemplary embodiment of FIG. 10, the diameter of the aperture 550 preferably is on the order of about 0.080 inches. (0.203 mm). The port 552 preferably is at a 45 degree angle with respect to the longitudinal axis of the heat generating element 536. Preferably the diameter of port 552 is about 0.007 inches. (0.018 mm).

Figure 11:
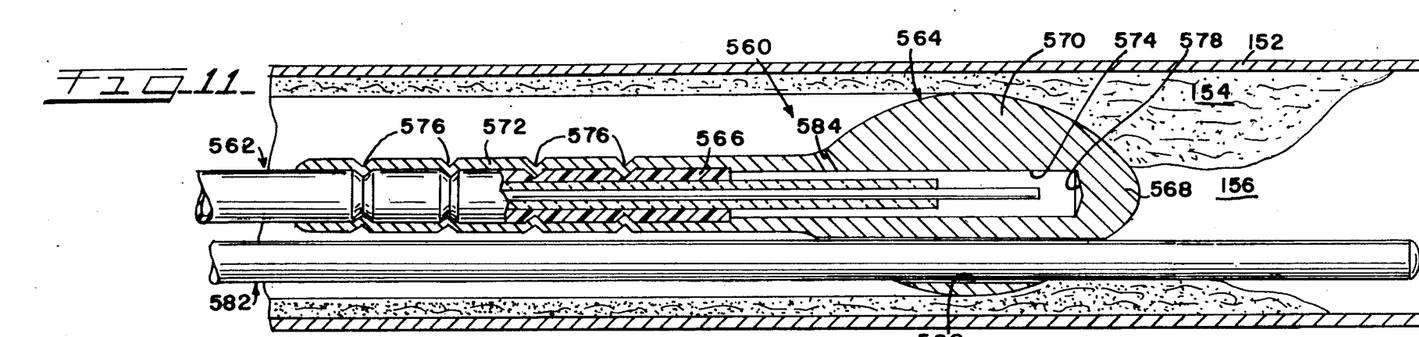
FIG. 11 is an enlarged cross-sectional view of a further embodiment of the medical device of FIG. 1 shown received within a blood vessel that has a constriction therein.

FIG. 11 illustrates another alternative embodiment of the medical device 10 as generally depicted in FIG. 1. The distal portion of medical device 560 is shown in FIG. 11 as an enlarged, fragmentary, sectional view. This portion of medical device 560 can be coupled to the remainder of the apparatus shown in FIG. 1 as described hereinabove. Medical device 560 includes a light transmitting fiber or conduit 562, of the same general nature as those utilized in the previously described embodiments of this invention, and a heat generating element 564 that is energized by a light beam that emanates from conduit 562 at its distal end 566.

Heat generating element 564 is eliptically shaped and is constituted by a curved head portion 568, and a balbous body portion 570 that tapers into a unitary sleeve portion 572 that together define a central cavity 574. Heat generating element 564 is mechanically coupled to conduit 562 at its distal end 566 by means of a plurality of peripheral mechanical crimps 576 in sleeve portion 572 which crimps correspond to the locking means 34 and 36 shown in FIG. 2. If desired, an adhesive can also be applied between the distal end 566 and the region of sleeve portion 572 bounded by mechanical crimps 576.

The wall thickness of the head portion 568 can be the same as or less than the wall thickness of the body portion 570. Preferably, the wall thickness of the head portion 568 is less than that of body portion 570 so as to concentrate more of the generated heat in the body portion 570. Because of the eliptical cross-section, the member 564 can be easily moved through the vascular system to the site of the obstruction. In addition, the smooth, tapered exterior surface facilitates movement into, through and back through the obstruction. Th eliptical cross-section of the heat generating member 564 is prefered in that it minimizes adhesion of atherosclerotic tissue. This adhesion is also minimized by preferably maintaining the operating temperature of the member 564 in a range of about 300° C. to about 500° C. and optimally about 400° C.

The heat generating member 564 receives radiant, or light energy through the optical fiber 562. The radiant energy impinges on at least an end surface or surfaces 578 that partly define cavity 574. The radiant energy impinging on the surface is 578 is converted to localized heat as discussed previously with respect to the previously illustrated embodiments. The generated heat is then transferred primarily by conduction, to the lumen obstruction 154.

The heat generating member 564 is assymetrical. An elongated channel 580 is formed in body portion 570 substantially parallel to the longitudinal axis of member 564. The channel 580 can be a cylindrical boring formed in the side wall 570 and the end 568. Alternately, the channel 580 can be a generally U-shaped slot. The channel 580 slidably engages a flexible guide wire 582 of a selected size and shape.

The elongated channel 580 can slidably engage the flexible guide wire 582 after the guide wire has been positioned within a selected lumen of the patient. The heat generating element 564 can then be slid along the guide wire 582, via cooperation between the channel 580 and the guide wire 582. When positioned, as discussed previously, radiant energy is applied through the light transmitting conduit 562 which in turn heats the heat generating element 564. Alternately, the guide wire 582 and the heat generating element 564 can be assembled together prior to insertion into the vascular system. The guide wire 582 in combination with the heating element 564 can be moved through the vascular system to the site of the obstruction.

The heat generating element 564 also includes a gas vent port 584 formed in body portion 570 adjacent the sleeve portion 572. The vent 584 provides for the escape or ventilation of gases formed in the cavity 574 as a result of the radiant energy applied to the heating element 564 through conduit 562. The vent 584 places the cavity 574 in fluid flow communication with the interior of the lumen into which the heating element 564 has been positioned. While the escape port or vent 584 may be formed in the body portion 570 at any convenient location, placing the vent 584 at about the juncture of sleeve portion 572 and the body portion 570 as illustrated in FIG. 11 insures that the escaping, relatively hot gases do not impinge directly upon the surrounding lumen but instead are diffused. The diameter of the heat generating element 564 can vary between 1.5 and 4.0 mm depending on the size of the lumen being treated.

Figure 12:
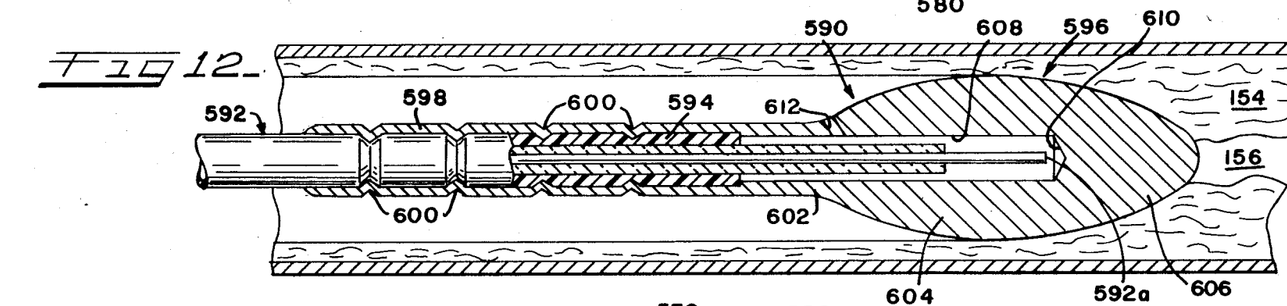
FIG. 12 is an enlarged cross-sectional view of another embodiment of the medical device of shown received within a blood vessel that has a constriction therein.

FIG. 12 illustrates another embodiment of the medical device 10 of FIG. 1. The medical device 590 shown in FIG. 12 in an enlarged, sectional, fragmentary view can be coupled to the other elements of the medical device 10 of FIG. 1. The medical device 590 includes an elongated light conducting or transmitting conduit 592 with a distal end 594 and heat generating element 596 that has an elongated, eliptical cross-section.

The distal end 594 is coupled to the heat generating element 596 at sleeve portion 598 by a plurality of mechanical crimps 600. In addition, adhesive may be used between the sleeve portion 598 and the distal end 594. The sleeve portion 598 is unitary with an elongated neck portion 602 that merges into a tapered body portion 604. The body portion 604 in turn terminates in a tapered, curved head portion 606. The tapered body portion 604 in combination with the head portion 606 results in a smooth exterior surface that easily slides through the vascular system.

As illustrated in FIG. 12, tapered body portion 604 has a varying side wall thickness and partly defines a cavity 608. The cavity 608 is also partially defined by the head portion 606 and the sleeve 598. The thickness of the side wall of body portion 604 is less than the wall thickness of the head portion 606.

The light transmitting fiber 592 emits light or radiant energy from an end surface 592a which impinges upon a surface 610 formed within head portion 606 at one end of the cavity 608. As discussed earlier with respect to the embodiments of FIGS. 1-8, radiant energy transmitted through the conduit 592 heats the heat generating element 596 when it impinges upon the surface 610. The application of heat to the obstruction 154 softens and destroys that destruction.

The heat generating element 596 also includes a gas vent, or port 612. The vent or port 612 extends through the body portion 604 of the heat generating element 596. The vent 612 provides an escape aperture for gases that may develop in the cavity 608.

Figure 13:
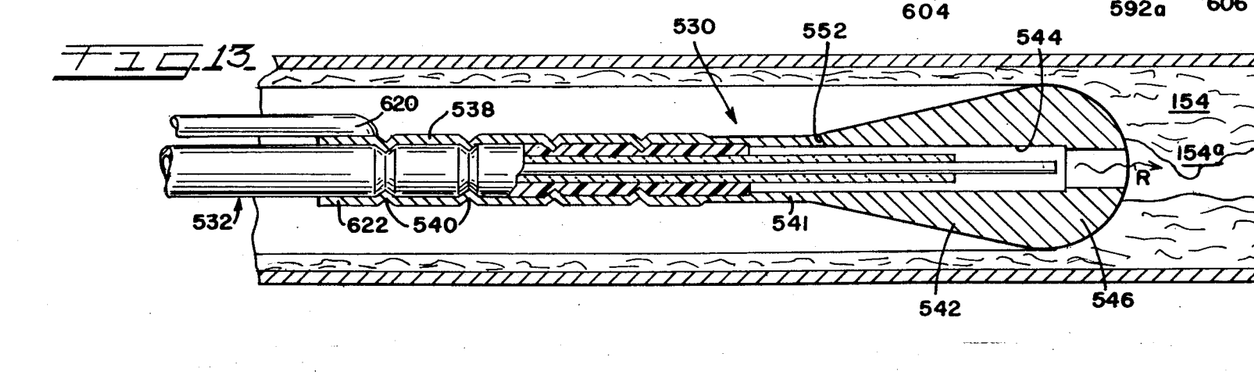
FIG. 13 is an enlarged cross-sectional view of a further embodiment of the medical device of shown received within a blood vessel that has a constriction therein.

FIG. 13 illustrates an alternate embodiment of the device 530 of FIG. 10. Elements in FIG. 13 that correspond to elements in FIG. 10 bear the same identification numeral designation as in FIG. 10. In the embodiment of FIG. 13, a solid wire 620 has been affixed to an end region 622 of the sleeve portion 538. The wire 620 can be affixed by brazing or welding or equivalent techniques. The wire 620 optimizes the handling characteristics of the heat generating element 536 without changing the characteristics of the fiber-optic member 532. If, for example, a "stiffer" instrument is desired for a certain procedure, a larger diameter wire can be used. The wire 620 will maintain the integrity of the instrument in the unlikely event that the fiber-optic member 532 and the heat generating element 536 separate during the treatment.

The alternate embodiments of FIGS. 9, 10, 11 and 12 can also be combined with structures from the embodiments of FIGS. 3-5 or 13. For example, the expandable cuff or balloon 166 of FIG. 3 could be combined with either the embodiment of FIG. 9 or the embodiment of FIG. 10. The window 546 and the port 550 could be combined with the heat generating elements 506, or 596 of FIG. 9, 12 or 13, respectively. The gas escape vents for the various embodiments previously discussed have a size and orientation corresponding to that of the vent 552 of FIG. 10.

Tests were conducted to determine the steady state thermal or heating characteristics of heat generating elements of the type previously discussed. Tests were also conducted in air and in selected tissue to determine the dynamic thermal characteristics of such heat generating elements. Temperature measurements were made using thermocouples affixed to respective heat generating elements.

Figure 14:
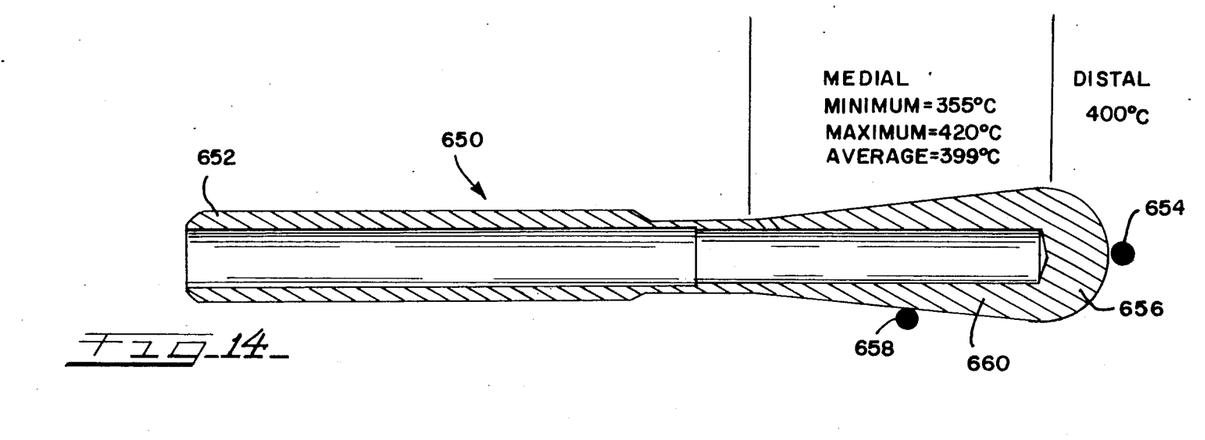
FIG. 14 is a schematic representation of a heat generating element with thermocouple attached thereto for equilibrium measurement of distal end and medial region temperatures.
Figure 15:
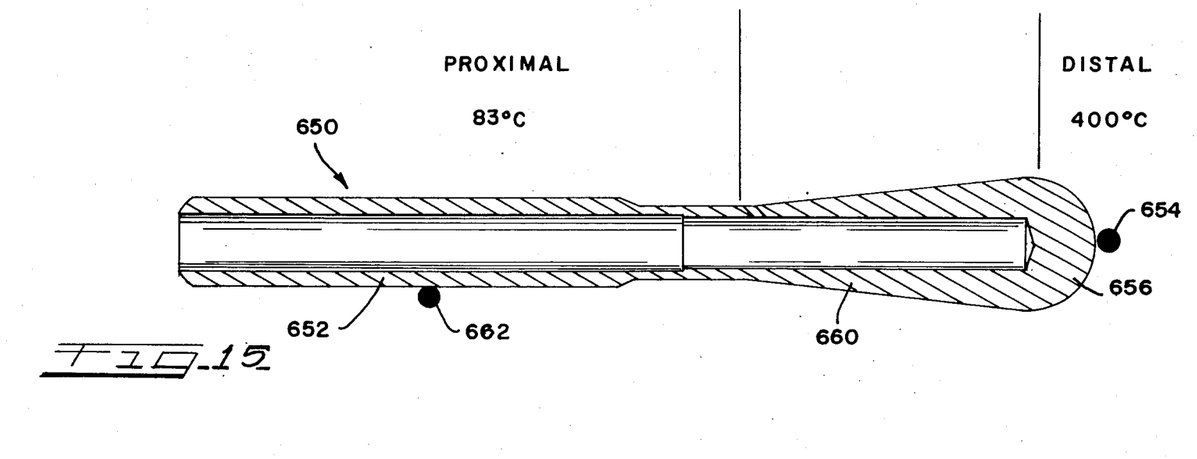
FIG. 15 is a schematic representation of a heat generating element with thermocouples attached thereto for equilibrium measurement of distal end and proximal end temperatures.

FIG. 14 illustrates a heat generating element 650 of the general type discussed previously. A fiber-optic member, not shown, was affixed to a proximal end 652 of the element 650. For the purpose of determining the steady state thermal characteristics of the distal end 656 and the medial region 660 of the element 650 in air, a thermocouple 654 was affixed to a distal end 656 of the element 650. A second thermocouple 658 was affixed to a medial region 660 of the element 650. FIG. 15 illustrates the same general type of heat generating element 656 as in FIG. 14. In FIG. 15 however, a thermocouple 662 has been affixed to the proximal end 652 to provide proximal end steady state temperature measurements of the element 650.

The laser source used to heat the element 650 was a Trimedyne/Laser Ionics model 555A 12-watt continuous-wave argon-ion laser. The laser was coupled to the element 650 through a fiber-optic member of the type discussed above. The thermocouples 654, 658 were fabricated from 0.010" chromel and alumel thermocouple wires (type "K"). Thermocouple junctions were formed and attached to the surface of the element 650, as shown in FIGS. 14, 15 by means of a "Hot Spot" thermocouple welder manufactured by DCC Corp. Tissue temperature readings were made with an Omega Engineering Model HYP-O Type "T" (Copper-Constantan) hypodermic thermocouple probe. Direct temperature readings were obtained from an Omega Engineering Model 2168A Digital Thermometer, calibrated with an Omega Engineering Model CL-300 Thermocouple Calibrator. Strip charts were generated using a Soltec Model Vp-67235 strip chart recorder. Thermocouple voltage level readings were taken using a Simpson Model 461 Digital Multimeter coupled to the thermocouples 654, 658.

To determine the medial region steady state temperature ranges, five heat generating elements, corresponding to the element 650, were excited with the laser. The laser was adjusted such that, in each instance, the temperature of the corresponding distal end 656 was 400° C. Measurements were then made of medial region temperatures. The range of recorded medial region temperatures was from 355° C. to 420° C. The average steady-state medial region temperature for the five tested heat generating elements was 399° C.

Steady state temperature measurements were made of the proximal end 652 of each of five heat generating elements positioned in a tissue sample wherein the laser had again been adjusted to provide a steady-state distal end temperature of 400° C. To conduct this thermal mapping in tissue, thermocouples 654, 662 were attached at the distal end 656 and the proximal region 658 as illustrated in FIG. 15. A lateral incision approximately ¾" (1.9 cm) deep was made in a fibrous tissue sample approximately 1" thick. (2.5 cm). The element 650 and attached thermocouple assembly were inserted into the incision in the tissue sample. The incision was closed around the element 650 and secured with two hemostats.

Figure 16:
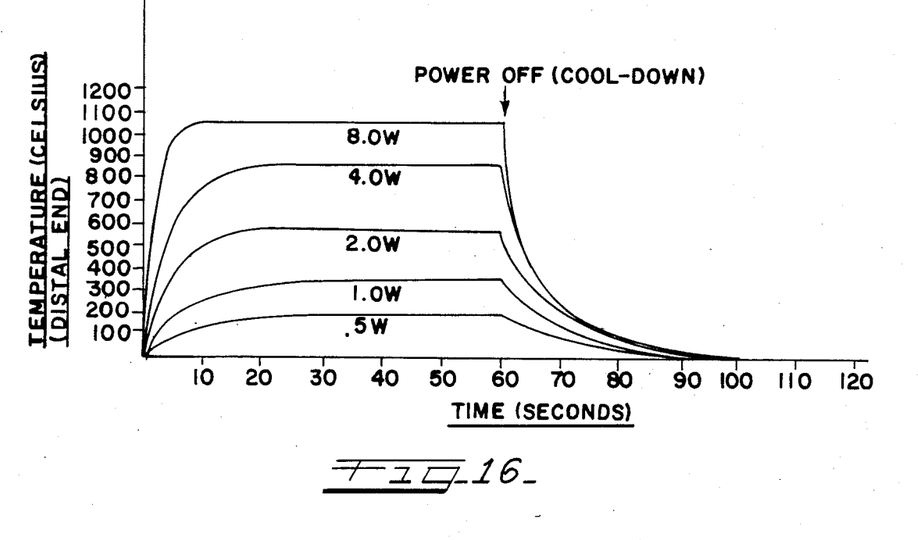
FIG. 16 is a graph of distal end temperature vs. time for various levels of input power.

The sample was then placed under water and the thermocouples 654, 662 were attached to a dual-channel strip chart recorder. The laser was activated in continuous wave mode until temperature of the distal end 656 reached 400° C. The laser energy was then modulated to maintain 400° C. at the distal end 656. The corresponding equilibrium temperature of the proximal section was then noted and recorded. The results of five such sets of tests are illustrated in FIG. 16. The average proximal section temperature was 83° C.

The steady state temperature of the distal end 656 of the heat generating element 650 was thus practically equivalent to that of the medial section 660 thereof. However, the steady state temperature of the proximal section 652 was substantially lower due to the distribution of material along the axis of the heat generating element 650. The design of the heat generating element 650 thus allows the thermal energy to be concentrated in the medial and distal sections 660, 656 thereof making it most effective for penetration and withdrawal while allowing the proximal section 662 thereof to remain relatively cool.

Tests were also conducted to determine the dynamic temperature response in air of the element 650 at various power levels. The thermocouples 654, 658 were attached to the strip chart recorder input for these tests. The baseline reference of the recorder was adjusted to compensate for ambient temperature, in this case 25° C., which put the baseline at 1.0 mV. For measurements in air and tissue, the 100 mV full scale range was used.

Voltage-to-temperature conversions were made using current reference tables superseding N.B.S. Circular #561. Chart speed was 8 cm./min.

For tests conducted with the element 650 in air, exposure and cool-down times of 1 minute were used. Input power was increased from 0.5 watts to 8 watts in 0.5 watt increments.

Thermal response curves for a 1.5 mm heat generating element 650 in air are shown in FIG. 16. Average values of equilibrium temperature and rise time at each power setting are given in Table I.

From FIG. 16 it can be seen that the time required for the heat generating element to reach thermal equilibrium in air as well as the required time required to return to base temperature is of the order of a few seconds. Distal end temperatures ranged from 191° C. at 0.5 watts to 1040° C. at 8 watts, with rise times ranging from 11.0 seconds down to 2.8 seconds, respectively, are shown in Table I. As illustrated in FIG. 16, in air, increasing the input power to the heat generating element 650 will cause that element to move from a lower, stable, distal end temperature to higher, stable, distal end temperature.

TABLE I

THERMAL RESPONSE DATA FOR 1.5 MILLIMETER HEAT GENERATING ELEMENT IN AIR

| $P_i$ | $T_e$ | $T_r$ |
|---|---|---|
| .5 | 191 | 11.0 |
| 1.0 | 342 | 8.1 |
| 1.5 | 485 | 7.4 |
| 2.0 | 580 | 5.7 |
| 2.5 | 678 | 6.2 |
| 3.0 | 758 | 5.5 |
| 3.5 | 802 | 4.7 |
| 4.0 | 837 | 4.5 |
| 4.5 | 893 | 4.0 |
| 5.0 | 924 | 3.4 |
| 5.5 | 954 | 3.1 |
| 6.0 | 972 | 3.0 |
| 6.5 | 992 | 2.9 |
| 7.0 | 1011 | 2.8 |
| 7.5 | 1025 | 2.5 |
| 8.0 | 1040 | 2.8 |

$P_i$ = Input power in watts
$T_e$ = Distal end temperature at equilibrium in degrees Celsius.
$T_r$ = Time to reach 63 percent of $T_e$ in seconds Data shown above are averages from results of testing five identical heat generating elements.

Tests were also conducted to determine the thermal response of the element 650 while passing through tissue in water. Tissue placed in water was used in this test to attempt to simulate conditions within a corporal body. For purposes of this test, the bare thermocouple leads near the thermocouple junctions were treated with an insulating coating to prevent the moisture from shorting them. Fibrous tissue approximately 2-2.5 cm thick was used. The thermocouple leads were attached to a needle and threaded through the tissue until the surface of the distal end 656 of the element 650 was in contact with the tissue. The thermocouple leads were then removed from the needle and attached to the strip chart recorder. The tissue sample and the element 650 were then submerged under water and the laser activated. Contact pressure of the element 650 was controlled by the flexibility of the optical fiber, thus allowing the element 650 to self-regulate the advancement rate through the tissue. After the element 650 had passed completely through the tissue, it was pulled back through the now existing channel. After each pass, the element 650 was activated in air to burn off any surface debris.

Tissue temperature measurements were made using a Type "T" (copper-constantan) hypodermic thermocouple probe attached to a digital thermocouple with built-in ice point reference. Several heat generating elements, corresponding to the element 650, were advanced through tissue samples using the same method as described above. Each of the heat generating elements was advanced approximately half-way through the tissue sample. Input power was then adjusted to yield a temperature of 400° C. at the distal end 656. The tissue sample was then probed with the hypodermic thermocouple until the thermocouple probe contacted the element 650. The thermocouple probe was then withdrawn approximately 1.5 mm and the reading at that point was recorded while the element 650 was activated.

Dynamic distal end temperature variations as the heat generating element 650 was pushed through the tissue sample, as discussed above, are illustrated in FIG. 17. From FIG. 17 it can be seen that at a nominal, recommended, distal end temperature of 400° C., typical input power for the condition of tissue ablation under water was approximately 9 watts and rise time was approximately 11 seconds when utilizing the 1.5 millimeter heat generating element. (Note that rise time is 63 percent of time to reach final temperature of 400° C.)

Figure 17:
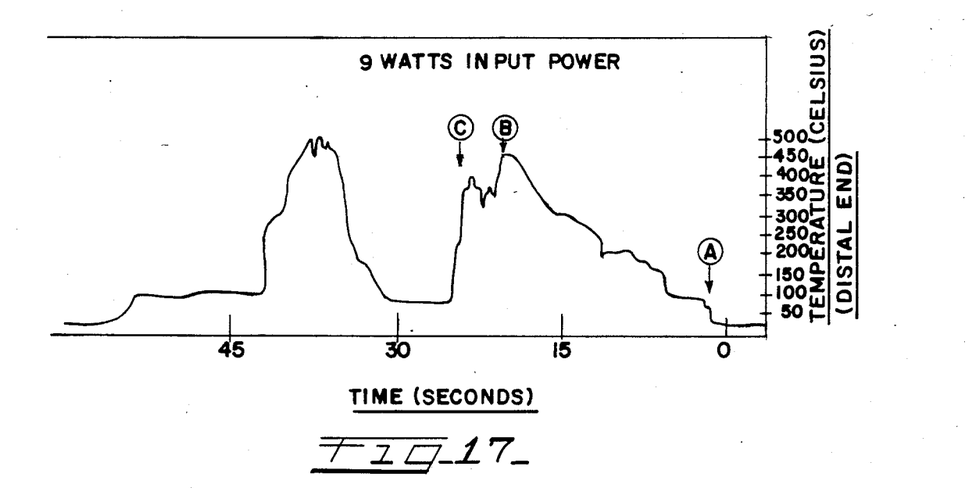
FIG. 17 is a graph of distal end temperature vs. time, with constant power input, generated as a heat generating element was pushed into and pulled back through a tissue sample under water.

FIG. 17 also illustrates the distal end temperature excursions produced during tissue penetration under water. The temperature of the distal end 656 typically rises very rapidly to 100° C. as the distal end 656 is pushed into the tissue sample. Once the interface moisture between the distal end surface and tissue vaporizes, the distal end temperature begins to rise (point A) and continues to rise as the distal end penetrates deeper into the tissue sample. The upper limit of surface temperature of the distal end 656 is determined by the input power to the heat generating element. As the distal end 656 approaches the other side of the tissue sample, the temperature starts to decline, (point B), until the distal end 656 once again comes in contact with free water (point C) at which point the temperature thereof rapidly returns to 100° C. until the laser is turned off. At this point, the surface temperature of the distal end 656 readily drops to ambient temperature. The second region of FIG. 17 shows the temperature changes of the distal end 656 as the heat generating element is pulled back through the newly created channel in the tissue sample. Penetration time was 25 seconds at 9 watts. The temperature excursions shown in FIG. 17 were largely due to such influences as tissue moisture content, probe pressure against the tissue, and advancement rate.

Tests were also carried out to measure the effectiveness of the medical device on artery walls. A particularly surprising result of those experiments was the relative thermal insulation provided by an artery. It was found that a substantial temperature gradient existed across the wall of the artery when the device was used. This demonstrates that it is possible to remove an obstruction within an artery using the medical device of the present invention with a minimum amount of trauma to the surrounding tissue.

The medical device embodying this invention can be used to deliver localized heat within a lumen such as a blood vessel. The heat can be used to open a clot or soften and remove plaque and fatty deposits which are found in blood vessels. The heated element softens the deposit material so that the element may be pressed into and through the plaque to enlarge the channel in a constriction or create a channel through an obstruction. This produces a relatively smooth, uniform channel having a diameter which is controlled by the size of the heat generating element used. Clotting and regrowth of tissue is minimized by such a smooth, uniform channel. It is also possible to make a series of passes through the same obstruction or constriction to create an even larger channel.

ANIMAL EXPERIMENT RESULTS

Bilateral cut-downs were performed on the femoral and carotid arteries of a male Shepherd-mix dog 82 pounds in weight. A Med 400 fiber having a stainless steel heat generating element mounted on the end as described above was inserted into the artery and positioned adjacent two of three sutures located in the right femoral artery to serve as markers. An Argon laser at a power level of 6 watts was used for 5-second bursts. The temperature increase of the artery and the heated element were measured in separate tests in the same artery. The thermocouple temperature probe located in the artery wall adjacent the heat generating element showed a temperature of 44 degrees C. after use of the laser from a base line temperature of 31.5 degrees C. In a second test the temperature of the heat generating element was measured after laser use at 66 degrees C. from a base line temperature of 34 degrees C.

Similar measurements were also made in the left femoral artery with the Argon laser at a power level of 6 watts, but using a two second burst. In the first test the temperature of the arterial wall increased from a base line temperature of 32 degrees C. to 36 degrees C. In the second test the temperature of the element within the artery increased from a base line temperature of 32.5 degrees C. to a final temperature of 47 degrees C. As can be seen, the artery has particularly good insulating qualities which protect the surrounding tissue.

Studies were also made of the effect of the heat generating element on the arterial wall itself. In these studies, the carotid arteries were exposed and for each artery three separate measurements were made at three different sites along the artery. For each measurement the temperature probe was located within the blood vessel to measure the temperature of the blood adjacent the heat generating element. Measurements of the outside diameter of the artery were made both before lasing and after lasing.

In the first set of tests, blood flow in the right carotid artery was stopped above and below the element by purse string sutures to simulate either a full occlusion by deposit or by the use of blood occlusion means such as a balloon. The results of those tests are set forth below in Table II. The one second burst measurement is believed to be a result of a measurement error due to either a "spike" in the heat gain or malposition of the probe.

TABLE II

| Laser Duration (Secs) | Baseline O.D. Of Vessel | | Final O.D. of Vessel | |
|---|---|---|---|---|
| | Temp (°C.) | Pre-Lasing (mm) | Temp (°C.) | Post-Lasing (mm) |
| 1 | 29 | 5.2 | 138 | 5.2 |
| 2 | 28 | 5.3 | 87 | 4.0 |
| 3 | 25 | 5.1 | 89 | 4.1 |

In a similar test, the left carotid artery was exposed and subjected to heating by the element. However, no purse string sutures were used to occlude the blood flow and the Argon laser was set at a power level of 6.4 watts. The results are set forth below in Table III.

TABLE III

| Laser Duration (Secs) | Baseline O.D. Of Vessel | | Final O.D. of Vessel | |
|---|---|---|---|---|
| | Temp (°C.) | Pre-Lasing (mm) | Temp (°C.) | Post-Lasing (mm) |
| 1 | 38 | 5.0 | 38 | 5.1 |
| 2 | 37 | 5.0 | 36 | 5.0 |
| 3 | 38 | 4.8 | 40 | 4.9 |

As can be seen from the above studies of arteries in a dog, the heat generating element can be raised to a sufficient temperature to soften a deposit such as a fat without extensive damage to an artery. It has also been demonstrated that the insulation quality of arterial wall substantially reduces trauma to any adjacent tissue.

Angiographic tests have been conducted with both dogs and rabbits in order to assess the in vivo dissolution of atherosclerotic obstructions therein as a result of using heat generating elements of the type previously described. Tests were conducted on 24 New Zealand white rabbits in which significant atherosclerosis had been induced. 0.2 mm fiber-optic members each with a 400 micron light transmitting core were used with and without heat generating elements of the type previously described.

Twelve rabbits were treated at sites of high-grade iliac stenosis with a fiber-optic member which did not have a heat generating member attached. With respect to this group of rabbits, the light generated by a laser coupled to the proximal end was permitted to radiate from the distal end of the fiber optic member and directly impinge onto the blockage in the vessel. Energy pulses of 1 watt for one second were delivered from the distal end of the fiber-optic member.

Twelve rabbits were treated at sites of high grade iliac stenosis with a fiber-optic member which had a heat generating element of the type discussed previously attached to the distal end thereof. With respect to this group of rabbits, the radiant energy generated by the laser heated the heat generating member, as previously discussed, thereby generating heat which was transferred primarily by conduction to the blockage in the vessel. Three-fifteen energy pulses of 6 watts for two seconds duration were delivered to the fiber-optic member.

During both sets of tests, laser pulses were delivered, while the fiber-optic member was being advanced, to two to four sites one centimeter apart. The results of the tests indicate that successful recanalization can be obtained through the use of the heat generating element. In 8 of the 12 rabbits so treated, the mean percent stenosis before treatment was 68 percent. This represented a substantial occlusion in each instance. After treatment with the heat generating element, the mean percent stenosis was reduced to 13 percent. This represented a substantially smaller occlusion. On the other hand, a reduction in vessel stanosis was noted in only two of the 12 rabbits that were treated with directly applied radiant energy. These reductions were lesser, 50 percent stenosis to 30 percent.

Vessel perforations were substantially less in the rabbits that were treated with the heat generating member, only one occurence out of twelve, as opposed to those rabbits that were treated with directly applied radiant energy in which nine occurences were observed out of twelve treatments.

Histological results for the two forms of treatment were strikingly different. With respect to those rabbits that received directly applied radiant energy, deep but localized laser generated defects were observed in the vessel walls. These defects extended through the neoitima and into the media. The laser induced defects resulted in minimal increases in lumen area because they were so localized. In addition, for ten of the twelve rabbits so treated, a considerable amount of thrombus formation was noted.

On the other hand, the vessels of those rabbits treated with the heat generating element disclosed a much more even reduction of the blockage about the inner circumference of the vessel. This appears to be due to the even circumferential distribution of heat energy about the heat generating element which in turn was transmitted to a larger, circumferential, interior surface of the vessel. Any noted thrombus was thinner than in the case of directly applied radiant energy. The zone of thermal effects in the twelve rabbits so treated was restricted to the neointima. No damage to the media or external elastic lamina and adventities was noted. These results have been reported in an article entitled: "Experimental Angioplasty: Circumferential Distribution of Laser Thermal Energy With a Laser Probe" by Sanborn et al., Vol. 5, No. 4, Journal of the American College of Cardiology. That article is hereby incorporated by reference.

Similar tests were conducted with a group of five large mongrel dogs (22-25 kg.). The results were consistent with those observed in the previously discussed rabbit tests. In addition, one of the dogs, at one occluded site was treated with an enlarged heat generating member, such as the member 11 of FIG. 3, as opposed to a member, such as the member 18 of FIG. 2, that has a diameter comparable to the diameter of the fiber-optic member 12. In this instance, a 1.5 mm diameter heat generating element was affixed to a 0.8 mm fiber-optic member. The resultant recanalization created or much wider channel than was the case with using either the fiber-optic member without a heat generating element or using the fiber-optic member with a heat generating element having a comparable diameter to the fiber-optic member. These results have been reported in an article entitled: "'Hot Tip': Another Method of Laser Vascular Recanalization" by Abela et al. Lasers In Surgery & Medicine, Volume 5, pp. 327-335, 1985, that article is hereby incorporated by reference.

Experience indicates that best results seem to be achieved when the heat generating member has an operating temperature on the order of 400° C. This operating temperature appears to be high enough to vaporize most, if not all, types of atherosclerotic plaque.

Thermal angioplasty using heat generating elements of the type discussed above has been succussfully completed in five human patients. Four of the patients exhibited femoral stenoses. The fifth patient exhibited popliteal total occlusion. Heat generating elements having an eliptical cross-section, such as the element 596 of FIG. 12, with a 2.0 mm diameter were used. The elements were heated with repeated 2-5 second pulses of 6-8 watts power generated by an argon laser.

A significant increase in angio-graphic lumen diameter, from 0.6±0.4 mm to 1.9±0.2 mm was observed for all patients. For three of the patients, balloon angioplasty was subsequently used to further increase the respective lumen diameter to 3.3±0.4 mm. Hence, thermal angioplasty can be a safe, effective adjunct or alternative to balloon angioplasty.

From the foregoing, it will be observed that numerous variations and modifications may be effected without departing from the true spirit and scope of the novel concept of the invention.

What is claimed is:

1. A localized heat applying medical device for applying heat to a site in a selected lumen and usable with a guide wire, the device comprising in operative association:
    (a) a flexible elongated light transmitting fiber having a proximal end and a distal end, the distal end being adapted to emit light transmitted by the fiber;
    (b) a metal heat generating element defining a cavity into which the distal end of the fiber is positioned and a light receiving surface adapted to collect at least a part of the light emitted by the distal end of the fiber, the element converting the collected light into heat;

(c) means, carried by the heat generating element, for engaging the guide wire such that the element can be positioned at the site; and (d) means for affixing the element to the distal end of the fiber such that at least part of the light emitted by the distal end is received on the surface of the element.

2. The medical device of claim 1 wherein the means for affixing the element includes locking means having an inwardly extending ridge on the element received in a groove defined by the light transmitting fiber.

3. The medical device of claim 1 wherein the light receiving surface bears a coating that enhances the coefficient of emissivity thereof.

4. The medical device of claim 1 including the guide wire the wire being engaged by the engaging means.

5. The medical device of claim 4 wherein the guide wire is a rigid wire affixed to an end of the element.

6. The medical device of claim 1 wherein the engaging means includes a channel for slidably receiving the guide wire.

7. The medical device of claim 1 wherein the heat generating element is hollow and includes a selectively located vent to permit a flow of gases from an interior region of the heat generating element to the exterior thereof.

8. The medical device of claim 1 wherein the heat generating element includes a selectively shaped bore oriented so as to permit selective amounts of light to pass therethrough and to impinge on a selected region within the lumen.

9. The medical device of claim 8 including optically transparent means for blocking an inflow of bodily material into the cavity.

10. A system for applying heat to a body site within a selected lumen of a patient, the system comprising in operative association:

(a) a medical device including flexible, elongated guide wire means insertable into the lumen; an elongated light transmitting fiber having a proximal end and a distal end, a heat generating element mounted with respect to the distal end such that light transmitted by the fiber to the element is converted into heat by the element, and means, carried by the heat generating element, for engaging the elongated guide wire means such that the element may be selectively positioned within the lumen; and (b) a radiant energy source associated with the proximal end of the fiber for providing sufficient radiant energy of sufficient intensity to raise the temperature of the element above the body temperature of the patient.

11. The system of claim 10 wherein the radiant energy source is a laser.

12. The system of claim 10 including temperature sensing means for measuring the temperature of the element.

13. The system of claim 12 wherein the radiant energy source and the temperature sensing means are associated with the proximal end of the fiber by a beam splitting means.

14. The system of claim 10 wherein the guide wire means is formed as an elongated cylindrical guide member slidable into and through the selected lumen.

15. The system of claim 14 wherein the engaging means is positioned at a proximal end of the heat generating element and fixedly attaches a distal end of the wire thereto.

16. The system of claim 14 wherein the engaging means slidably receives the guide wire.

17. The system of claim 16 wherein the engaging means includes a channel for receiving the wire.

18. The system of claim 10 wherein the heat generating element is hollow and includes a vent that permits a flow of gases from an interior region of the heat generating element to the exterior thereof.

19. The system of claim 10 wherein the heat generating element includes a channel oriented so as to permit a predetermined amount of light to pass therethrough and to impinge on a selected region within the lumen.

20. The system of claim 19 including optically transparent means for blocking an inflow of bodily fluid into an interior region of the heat generating element.

21. The system of claim 20 wherein the optically transparent means is a quartz window.

* * * * *